United States Patent [19]

Panzeri et al.

[11] Patent Number: 5,342,948
[45] Date of Patent: Aug. 30, 1994

[54] PROCESS FOR THE PREPARATION OF 17β-SUBSTITUTED-4-AZA-5α-ANDROSTAN-3-ONE DERIVATIVES

[75] Inventors: Achille Panzeri, Merate; Lucio Ceriani, Parabiago; Pierluigi Griggi, Monza; Marcella Nesi, Milan, all of Italy

[73] Assignee: Farmitalia Carlo Erba S.R.L., Milan, Italy

[21] Appl. No.: 27,164

[22] PCT Filed: Jul. 16, 1992

[86] PCT No.: PCT/EP92/01620
§ 371 Date: Mar. 19, 1993
§ 102(e) Date: Mar. 19, 1993

[30] Foreign Appliation Priority Data
Jul. 19, 1991 [GB] United Kingdom ............... 9115676

[51] Int. Cl.$^5$ .................. C07D 221/02; C07J 73/00
[52] U.S. Cl. .................................................. 546/77
[58] Field of Search ........................................ 546/77

[56] References Cited

U.S. PATENT DOCUMENTS

| | | | |
|---|---|---|---|
| 3,022,312 | 2/1962 | Wildi et al. | 546/77 |
| 4,220,775 | 9/1980 | Rasmusson et al. | 46/77 |
| 4,377,584 | 3/1983 | Rasmusson et al. | 546/77 |
| 5,110,939 | 5/1992 | Holt et al. | 546/77 |
| 5,155,107 | 10/1992 | Panzeri et al. | 546/77 |

FOREIGN PATENT DOCUMENTS

| | | |
|---|---|---|
| 0004949 | 10/1979 | European Pat. Off. |
| 0155096 | 9/1985 | European Pat. Off. |

OTHER PUBLICATIONS

Back, J. Org. Chem vol. 46, pp. 1442–1446 (1981).
Edward et al. Can. J. Chem. vol. 30, pp. 590–591 (1961).
Steroids, vol. 46, No. 1 July 1985, San Francisco, US, pp. 655–676, G. Rapi, et al, "Reaction of Some Antiinflammatory 17-β(2-aminooxazol-4-yl) Steriods with Hydrogen Peroxide". Synthesis of Steriod-17-spiro-5-oxazolidine-2, 4-dione'.

Primary Examiner—Donald G. Daus
Attorney, Agent, or Firm—Oblon, Spivak, McClelland, Maier & Neustadt

[57] ABSTRACT

The preparation of a compound of formula (I)

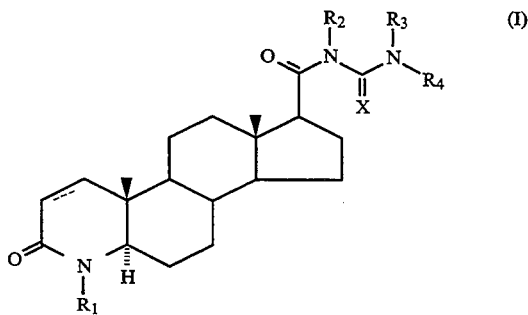

wherein X is oxygen or sulphur; $R_1$ is hydrogen or $C_1$–$C_6$ alkyl; each of $R_2$ and $R_3$ is, independently, hydrogen, $C_1$–$C_6$ alkyl, $C_5$ or $C_6$ cycloalkyl or $C_6$–$C_9$ cycloalkylalkyl; $R_4$ is hydrogen, $C_1$–$C_6$ alkyl, $C_3$- or $C_6$cycloalkyl, $C_6$–$C_9$ cycloalkylalkyl or aryl; and the symbol ---- represents a single or a double bond; by a multi-step process is disclosed.

8 Claims, No Drawings

PROCESS FOR THE PREPARATION OF 17β-SUBSTITUTED-4-AZA-5α-ANDROSTAN-3-ONE DERIVATIVES

The present invention relates to the preparation of 17β-substituted-4-aza-5α-androstan-3-one derivatives.

17β-substituted-4-aza-5α-androstan-3-one derivatives bearing an acylureidic side chain at the 17β position are described in our copending application PCT/EP 91/00228. In this patent application the derivatives are synthesised by a process which involves introducing the acylureidic chain as the last step.

It has now surprisingly been found that the 17β-acylureidic group has an unexpected stability and a low reactivity. This means that reactions may be performed on the A-ring moiety of a steroid already bearing an acylureidic group without there being any adverse effect on the latter.

According to the present invention, there is provided a process for the preparation of a compound of formula (I)

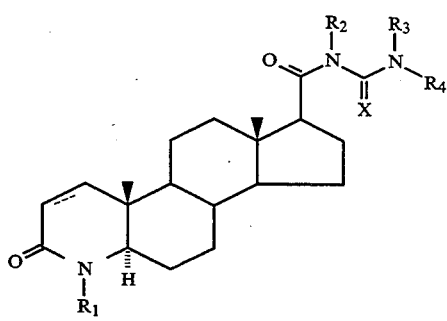

wherein X is oxygen or sulphur;

$R_1$ is hydrogen or $C_1$-$C_6$ alkyl;

each of $R_2$ and $R_3$ is, independently, hydrogen, $C_1$-$C_6$ alkyl, $C_5$-$C_6$ cycloalkyl, $C_6$-$C_9$ cycloalkylalkyl, $R_4$ is hydrogen, $C_1$-$C_6$ alkyl, $C_5$-$C_6$ cycloalkyl, $C_6$-$C_9$ cycloalkylalkyl or aryl; and the symbol - - - represents a single or a double bond, the process comprising:

a) oxidizing a compound of formula (II)

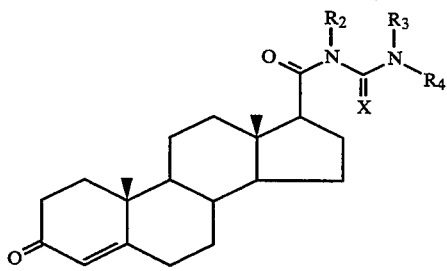

wherein X, $R_2$, $R_3$ and $R_4$ are as defined above, to obtain a compound of formula (III)

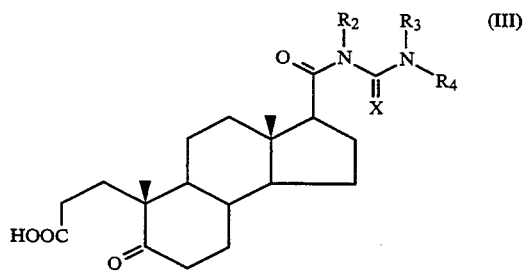

wherein X, $R_2$, $R_3$ and $R_4$ are as defined above;

b) reacting a compound of formula (III), as defined above, with a compound of formula (IV)

$R_1$—$NH_2$  (IV)

wherein $R_1$ is as defined above, to obtain a compound of formula (V)

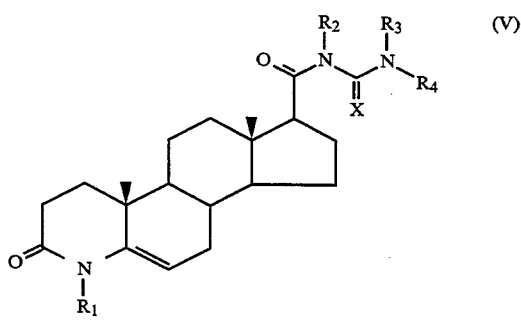

wherein X, $R_1$, $R_2$, $R_3$ and $R_4$ are as defined above;

c) reducing a compound of formula (V), as defined above, to obtain a compound of formula (I) wherein - - - - is a single bond, and X, $R_1$, $R_2$, $R_3$ and $R_4$ are as defined above;

d) optionally dehydrogenating a compound of formula (I) wherein - - - - is a single bond and X, $R_1$, $R_2$, $R_3$ and $R_4$ are as defined above to obtain a compound of formula (I) wherein - - - - is a double bond and X, $R_1$, $R_2$, $R_3$ and $R_4$ are as defined above; and/or, if desired, e) optionally separating a mixture of isomers into the individual isomers.

An advantage of the process of the invention is that the presence of the acylureidic side chain in the precursors (intermediates) makes these more readily purifiable by crystallization. This enables any trace of unreacted intermediate in the final product to be avoided. Another remarkable advantage is that, by reducing the 5,6-double bond of a compound which already contains the β-acylureidic side chain, in accordance with the process of the invention, no 5β-reduced side-product is obtained.

In the formulae of this specification the dotted line ( ) indicates a substituent in the α configuration, i.e. below the plane of the ring, and the wedged line (◂) indicates a substituent in the β configuration, i.e. above the plane of the ring.

In this specification the alkyl groups and the aliphatic portions of the arylalkyl and cycloalkylalkyl groups may be straight or branched chain.

$R_1$ is preferably hydrogen or a methyl or ethyl group.

Each of $R_2$ and $R_3$ is preferably hydrogen, methyl, ethyl, isopropyl, tert-butyl, tert-butylmethyl, cyclohexyl or cyclohexylmethyl. $R_4$ is preferably hydrogen, methyl, ethyl, isopropyl, n-butyl, isobutyl, tert-butyl, tert-butylmethyl, cyclohexyl, cyclohexylmethyl, phenyl or 2,6-dichlorophenyl; most preferably $R_4$ represents a hydrogen atom.

Examples of preferred compounds obtained by the process of the invention are:

1) 1-[4-methyl-3-oxo-4-aza-5α-androstane-17β-carbonyl]1,3-diisopropylurea;
2) 1-[3-oxo-4-aza-5α-androst-1-ene-17β-carbonyl]-1,3-diisopropylurea;
3) 1-[3-oxo-4-aza-5α-androstane-17β-carbonyl]-1,3-diisopropylurea;
4) 1-[4-methyl-3-oxo-4-aza-5α-androstane-17β-carbonyl]-1,3-diisopropylthiourea;
5) 1-[3-oxo-4-aza-5α-androstane-17β-carbonyl]-1,3-diisopropylthiourea;
6) 1-[4-methyl-3-oxo-4-aza-5α-androstane-17β-carbonyl]-1,3-dicyclohexylurea;
7) 1-[3-oxo-4-aza-5α-androst-1-ene-17β-carbonyl]-1,3-dicyclohexylurea;
8) 1-[3-oxo-4-aza-5α-androstane-17β-carbonyl]-1,3-dicyclohexylurea;
9) 1-[4-methyl-3-oxo-4-aza-5α-androstane-17β-carbonyl]-1,3-dicyclohexylthiourea;
10) 1-[3-oxo-4-aza-5α-androstane-17β-carbonyl]-1,3-dicyclohexylthiourea.

The oxidation of a compound of formula (II) may be carried out, for example, in the presence of an oxidising agent such as sodium metaperiodate and potassium permanganate in an organic solvent and a base such as aqueous potassium carbonate. It is suitably performed at a temperature of from room temperature to about 60° C., typically for a period of from about one hour to about five hours.

Preferably the organic solvent is methanol, ethanol, acetone, tetrahydrofuran, dioxane, isopropanol, tert-butanol or a mixture of any of these.

The reaction is suitably performed by adding a solution of the oxidising agent, for example, sodium metaperiodate and potassium permanganate, and the base such as potassium carbonate, in water to a solution of a compound of formula (II) in an organic solvent, or by adding simultaneously an aqueous solution of sodium metaperiodate and an aqueous solution of potassium permanganate to a solution of a compound of formula (II) in an organic solvent and aqueous potassium carbonate.

Alternatively the oxidation of a compound of formula (II) may be carried out with ozone in an organic solvent. The reaction is typically continued until all the starting material is consumed. The temperature of the reaction is suitably from about $-78°$ C. to room temperature. An oxidising agent is then added to the reaction mixture to destroy the resulting ozonide. Preferably, the solvent is methylene chloride, ethylacetate, methanol or a mixture of any of these. The oxidising agent is preferably hydrogen peroxide.

The reaction between a compound of formula (III) and a compound of formula (IV) is preferably carried out in an anhydrous organic solvent at a temperature from about 60° C. to the reflux temperature of the solvent. It is suitably continued for a period of from about 30 minutes to about four hours.

Preferably the solvent is ethylene glycol, dimethylformamide, dimethylsulphoxide, ethanol, methanol, dioxane, ethylacetate or a mixture of any of these.

When the oxidation of a compound of formula (II) (step (b)) is carried out with ozone, it is possible to perform step (b) by treating directly the ozonide containing reaction mixture with the amine of formula (IV), typically in excess, thereby directly obtaining a compound of formula (V).

The reduction of a compound of formula (V) is preferably carried out in an organic solvent under hydrogen pressure varying from about 1 atom to about 10 atm, in the presence of hydrogenation catalyst. The temperature is typically from room temperature to about 100° C. The reduction time typically varies from about 30 minutes to about five hours.

Preferably the solvent is ethanol, acetic acid or a mixture of any of these and the hydrogenation catalyst is platinum oxide (Adams' Catalyst), 5% or 10% palladium on charcoal or palladium hydroxide.

The optional dehydrogenation of a compound of formula (I) is preferably carried out in an anhydrous organic solvent in the presence of a dehydrogenating agent. The temperature is suitably from room temperature to about the reflux temperature of the solvent, and the reaction time is typically from about 2 hours to about 24 hours.

Preferably the solvent is chlorobenzene, dioxane, diglyme, xylene, toluene or benzene, the dehydrogenating agent is chloranil, benzeenselenic anhydride or dichlorodicyano benzoquinone and the reaction is carried out under inert atmosphere.

Optionally the dehydrogenation reaction may be carried out in the presence of bis(trimethylsilyl) trifluoroacetamide.

A compound of formula (II) wherein $R_4$ is hydrogen and X, $R_2$ and $R_3$ are as defined above may be prepared by reacting a compound of formula (VI)

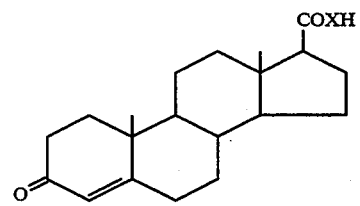

wherein X is as defined above with a compound of formula (VII)

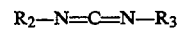

wherein $R_2$ and $R_3$ are as defined above, and, if desired, separating the individual isomers from the mixture of isomers which is obtained.

The reaction is preferably carried out in a suitable anhydrous organic solvent, optionally in the presence of an organic base, such as, for instance pyridine or triethylamine. The temperature is typically from 0° C. to the reflux temperature of the solvent and the reaction time is typically from about 2 hours to about 48 hours.

Suitable organic solvents include, for example, diethyl, ether, benzene, dioxane, methylene chloride, dimethylformamide, tetrahydrofurane and mixtures of any of these.

Alternatively a compound of formula (II) wherein X, $R_2$ and $R_3$ are as defined above and $R_4$ is hydrogen may be prepared reacting a compound of formula (VIII)

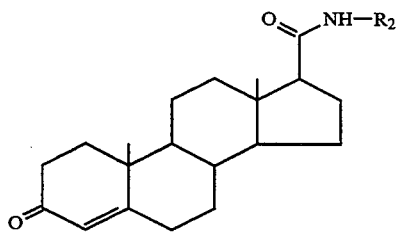

(VIII)

wherein R₂ is as defined above with a compound of formula (IX)

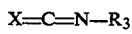

(IX)

wherein X and R₂ are as defined above.

Preferably the reaction is carried out in an organic solvent, at the reflux temperature of the solvent, under an inert atmosphere. The reaction time is typically from about 1 hour to about 48 hours.

The solvent is preferably dioxane, toluene, xylene or pyridine.

A compound of formula (II), wherein X, R₂, R₃ and R₄ are as defined above may be prepared reacting a compound of formula (X)

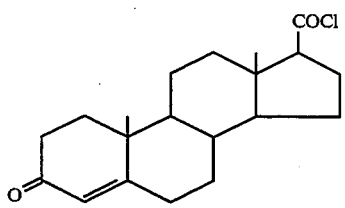

(X)

with a compound of formula (XI)

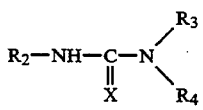

(XI)

wherein X, R₂, R₃, R₄ are as defined above.

Preferably the reaction is carried out in an anhydrous organic solvent in the presence of an organic base and, optionally, dimethylaminopyridine. The temperature is typically from about 0° C. to the reflux temperature of the solvent, and the reaction time is suitably from about 30 minutes to about 78 hours.

The solvent is preferably methylene chloride, dimethylformamide, tetrahydrofurane, benzene, toluene or a mixture of any of these.

Compounds (VI), (VII), (VII), (IX), (X) and (XI) are known compounds or can be obtained by known methods.

The compounds obtained by the process of the present invention inhibit specifically the testosterone 5α-reductase enzyme. They are therefore potent antiandrogens and are therapeutically useful in situations in which a selective decrease in androgen action, by means of 5α-reductase inhibition, is desirable. Examples include benign prostatic hyperplasia, prostatic and breast cancers and certain skin-hair conditions such as acne, seborrhoea, female hirsutism and male pattern baldness.

The following examples illustrate but do not limit the invention.

EXAMPLE 1

17β-[N-isopropyl-N(N'-isopropylcarbamoyl)carbamoyl]-5-oxo-4-nor-3,5-secoandrostan-3-oic acid 50 g of 1-[3-oxoandrost-4-ene-17β-carbonyl]-1,3-diisopropylurea, 750 ml of isopropyl alcohol and 88 ml of 2M sodium carbonate solution are loaded in a 21 four-necked flask equipped with a condenser, a thermometer, a dropping funnel and mechanical stirrer and the suspension is heated to about 60° C.

The obtained solution is treated with 150 ml of 2% potassium permanganate and 310 ml of 1,8M sodium metaperiodate added dropwise simultaneously over a period of 30 minutes.

The resulting suspension is stirred for one hour, then cooled to room temperature and filtered. The obtained solution is concentrated under vacuum up to about 600 ml, poured in 1000 ml of water under stirring and acidified to pH 3–4.

After 30' minutes stirring, the precipitate is collected by filtration, washed with water and dried under vacuum at 60° C., obtaining 45 g of title compound as a white solid (yield 86%)
m.p. 185°–186° C.

| Found: | C 67,06 H 9,23 N 5,96 | $C_{26}H_{42}N_2O_5$ |
|---|---|---|
| Requires: | C 67,50 H 9,15 N 6,05 | |
| $[\alpha]_D + 44°$ (C = 0.1 DMF) | | |

Following analogous procedure the below listed compounds can be obtained:

17β-[N-cyclohexyl-N-(N'-cyclohexylcarbamoyl)carbamoyl]-5-oxo-4-nor-3,5-secoandrostan-3-oic acid;

17β-[N-isopropyl-N-(N'-isopropylthiocarbamoyl)carbamoyl]-5-oxo-4-nor-3,5-secoandrostan-3-oic acid;

17β-[N-cyclohexyl-N-(N'-cyclohexylthiocarbamoyl)carbamoyl]-5-oxo-4-nor-3,5-secoandrostan-3-oic acid.

EXAMPLE 2

1-[4-methyl-3-oxo-4-aza-androst-5-ene-17β-carbonyl]-1,3-diisopropylurea

A suspension of 50 g of 17β-[N-isopropyl-N(N'-isopropylcarbamoyl)carbamoyl)-5-oxo-4-nor-3,5-secoandrostan-3-oic acid in 250 ml of dioxane is loaded into an autoclave, then 16 g of anhydrous methylamine are added under stirring at about 18° C.

When the addition is over the suspension is heated at about 80° C. for one hour and then cooled to room temperature.

After removing the excess of methylamine by nitrogen flow, the reaction solution is concentrated under vacuum up to 150 ml, and the resulting suspension is poured into 230 ml of water under stirring.

The obtained suspension if filtered and the precipitate washed with water. After drying under vacuum at about 60° C., 38 g of the title compound are obtained (yield —76.8%).
m.p. 152°–154° C.

| Found: | C 70,62 H 9,52, N 9,09 | |
|---|---|---|
| Requires: | C 70,86; H 9,47; N 9,17 | $C_{27}H_{43}N_3O_3$ |
| $[\alpha]_D - 110°$ (C = 0, 1 DMF) | | |

Following analogous procedures the below listed compounds can be obtained:

1-[3-oxo-4-aza-androst-5-ene-17β-carbonyl]-1,3-diisopropylurea;

1-[4-methyl-3-oxo-4-aza-androst-5-ene-17β-carbonyl]-1,3-dicyclohexylurea;

1-[3-oxo-4-aza-androst-5-ene-17β-carbonyl-1,3-dicyclohexylurea;

1-[4-methyl-3-oxo-4-aza-androst-5-ene-17β-carbonyl]-1,3-diisopropylthiourea;

1-[3-oxo-4-aza-androst-5-ene-17β-carbonyl]-1,3-diisopropylthiourea;

1-[4-methyl-3-oxo-4-aza-androst-5-ene-17β-carbonyl]-1,3-dicyclohexylthiourea;

1-[3-oxo-4-aza-androst-5-ene-17β-carbonyl]-1,3-dicyclohexylthiourea.

EXAMPLE 3

1-[4-methyl-3-oxo-4-aza-5α-androstane-17β-carbonyl]-1,3-diisopropylurea

A solution of 50 g of 1-[4-methyl-4-aza-androst-5-ene-17β-carbonyl]-1,3-diisopropylurea in 800 ml of absolute ethanol is treated with 29 g of 10% palladium on charcoal.

The resulting suspension is hydrogenate at about 100° C. under low pressure for about 4 hours, cooled to room temperature and filtered; the obtained solution is concentrated under vacuum and the resulting suspension is stirred for two hours under cooling.

After filtration the crude product is cristallized from 400 ml of ethyl acetate and 31 g of pure product are obtained (yield 61.2%).

| | | |
|---|---|---|
| Found | C = 70.46; H = 9.83; N = 9.03 | |
| Requires | C = 70.55; H = 9.87; N = 9.13 | $C_{27}H_{45}N_3O_3$ |
| $[\alpha]_D + 30°$ (C = 0.1, DMF) | | |

Following analogous procedure the below listed compounds can be prepared:

1-[3-oxo-4-aza-5α-androstane-17β-carbonyl]-1,3-diisopropylurea m.p. 210°–212° C.;

1-[4-methyl-3-oxo-4-aza-5α-androstane-17β-carbonyl]1,3-dicyclohexylurea m.p. 182°–183° C.;

1-[3-oxo-4-aza-5α-androstane-17β-carbonyl]-1,3-dicyclohexylurea m.p. 215°–217° C.;

1-[4-methyl-3-oxo-4-aza-5α-androstane-17β-carbonyl]1,3-diisopropylthiourea m.p. 167°–169° C.;

1-[3-oxo-4-aza-5α-androstane-17β-carbonyl]-1,3-diisopropylthiourea m.p. 179°–181° C.;

1-[4-methyl-3-oxo-4-aza-5α-androstane-17β-carbonyl]1,3-dicyclohexylthiourea;

1-[3-oxo-4-aza-5α-androstane-17β-carbonyl]-1,3-dicyclohexylthiourea.

EXAMPLE 4

1-[3-oxo-4-aza-5α-androst-1-ene-17β-carbonyl]-1,3-diisopropylurea

A mixture of 1-[3-oxo-4-aza-5α-androstane-17β-carbonyl]-1,3-diisopropylurea (306 mg) and benzeneseleninic anhydride (360 mg) in anhydrous diglyme (30 ml), are heated at 120° C. for 14 hours.

The solvent is removed in vacuo and the residue chromatographed on silica gel, eluting with methylene chloride/acetone 60/40, so obtaining 135 mg of the title compound;

m.p. 285°–287° C.;

| | | |
|---|---|---|
| Found: | C = 70.23  H = 9.31  N = 9.38 | |
| Requires: | C = 70.39  H = 9.32  N = 9.47 | $C_{26}H_{41}N_3O_3$ |

Following analogous procedures, the below listed compounds can be prepared:

1-[3-oxy-4-aza-5α-androst-1-ene-17β-carbonyl]-1,3-ditert-butylurea,
m.p. 273°–260° C. dec.;

1-[3-oxy-4-aza-5α-androst-1-ene-17β-carbonyl]-1,3-dicyclohexylurea.
m.p. 290°–292° C.

EXAMPLE 5

1-[3-oxo-androst-4-ene-17β-carbonyl]-1,3-diisopropylurea 50 g of methyl androst-4-en-3-one-17β-carboylate, 250 ml of methanol and a solution of 31 g of potassium hydroxide in 31 ml of water are loaded in a 1 l four-necked flask equipped with condenser, thermometer, mechanical stirrer, and the mixture is heated to reflux temperature for three hours under stirring.

After cooling to 10° C. the mixture is added with 250 ml of water and acidified to 4–5 pH under stirring. The suspension is then filtered and the cake is washed with water obtaining 100 g of dump product.

The dump product obtained is dissolved in 1300 ml of ethyl acetate and the solution is treated with 35 ml of triethylamine, 38 ml of N,N'-diisopropylcarbodiimide and heated to reflux temperature under stirring for one hour.

After cooling to 5° C. the suspension is filtered and the clear solution is firstly washed with acid solution, then with a basic solution and finally with water.

The organic phase, is concentrated to a final volume of about 500 ml and, after filtration and drying at 60° C. under vacuum, 60 g of the title compound are obtained (yield 86%) m.p. 172°–175° C.

| | | |
|---|---|---|
| Found: | C 73.29; H 9.58; N 6.30 | $C_{27}H_{42}N_2O_3$ |
| Requires: | C 73.26; H 9.56; N 6.33 | |
| $[\alpha]_D \pm 89°$ (C = 0.1, DMF) | | |

Following analogous procedure the below listed compounds can be prepared.

1-[3-oxo-androst-4-ene-17β-carbonyl]-1,3-dicyclohexylurea m.p. 178°–180° C., $[\alpha]_D+77°$ (C=1; DMF);

1-[3-oxo-androst-4-ene-17β-carbonyl]-1,3-ditertbutylurea m.p. 175°–177° C., $[\alpha]_D+53°$ (C=0.5; DMF) and 1-[3-oxo-androst-4-ene-17β-carbonyl]-1,3-diisopropylthiourea m.p. 180°–183° C., $[\alpha]_D+146°$ (C=1, DMF).

EXAMPLE 6

Methyl Androst-4-en-3-one-17β-carboxylate 745 ml of toluene 50 g of methyl androst-5-en-3β-ol-17βcarboxylate, 42 ml of cyclohexanone, in a 2 l four-necked flask and the mixture is heated to reflux temperature. After removing about 100 ml of toluene by distillation, a suspension of 50 g of aluminium 150 isopropoxide in 100 ml of toluene is added and the resulting mixture is heated at reflux temperature for 90 minutes.

The obtained suspension is cooled to 60° C. and washed firstly with 240 ml of 1N hydrochloric acid and then with 124 ml of water.

The organic phase is evaporated under vacuum and the residual solvent is removed by azeotropic distillation, firstly with 170 ml of water and than with 180 ml of toluene.

The solid residue obtained is washed in suspension with 190 ml of cyclohexane, the precipitate is collected by filtration and dried under vacuum at 60° C. obtaining 40 g of title compound (yield 80.5%).

m.p. 128°–130° C.

| Found: | C 76.28; H 9,05; | $C_{21}H_{30}O_3$ |
|---|---|---|
| Requires: | C 76.32; H 9.15; | |
| $[\alpha]_D$ — 152° (C = 0.1, DMF) | | |

EXAMPLE 7

Methyl androst-5-en-3β-ol-17β-carboxylate 50 g of Preg-5-en-3β-ol-20-one-21-pyridinium-iodide salt are added under stirring and under a nitrogen flow to a suspension of 6,7 g of sodium methylate in 250 ml of methanol. After heating for 90 minutes at reflux temperature the mixture is cooled to 10° C. and treated with 250 ml of water and 5 ml of 23% hydrochloridric acid obtaining a suspension.

The precipitate, collected by filtration, is washed in suspension with a mixture of isopropanol/water 70/30, then dried under vacuum at 60° C., obtaining 25 g of the title compound (yield 78.5%)

m.p. 175°–177° C.

| Found: | C 75.74; H 9.75 |
|---|---|
| Requires: | C 75.86  H 9.70 |
| $[\alpha]_D$ — 16° (C = 0.1 DMF) | |

EXAMPLE 8

Preg-5-en-3β-ol-20-one-21-pyridinium-iodide salt 50 g of Preg-5-en-3β-ol-20-one, 150 ml of pyridine and 60 g of iodine are loaded into a 500 ml four-necked flask equipped with condenser thermometer and mechanical stirrer.

The obtained mixture is heated at reflux temperature for 2 hours, then is cooled to 10° C. and treated with 150 ml of water.

The resulting suspension is stirred for 10 min. and the solid product, collected by filtration, is washed in suspension with 120 ml of acetone, filtered again and dried under vacuum at 60° C.; 65 g of the title compound (yield 80%) are obtained m.p. 243°–245° C. with decomposition.

| Found: | C 59.67; H 6.94; N 2.85 | $C_{26}H_{36}NO_2I$ |
|---|---|---|
| Requires: | C 59.88; H 6.96; N 2.68 | |
| $[\alpha]_D$ + 40° (C = 0.1 DMF) | | |

EXAMPLE 9

1-[3-oxo-androst-4-ene-17β-carbonyl]-3-tertbutylurea

To a mixture of androst-4-en-3-one 17β-carboxylic acid (95 mg) in anhydrous toluene (2 ml), oxalyl chloride (0.24 ml) is added slowly.

The mixture is stirred at room temperature for 30 min. and then the solvents are removed in vacuo without heating. The residue is dissolved in pyridine (1.36 ml) and then tert-butylurea (35 mg) is added.

After stirring for 2 hours, the reaction mixture is poured into ice water (20 ml) and extracted with methylene chloride. The combined organic extracts are washed with 1N hydrochloric acid, brine, water and dried over sodium sulphate.

Evaporation of the solvent leaves 0.110 g of a dark oil which is chromatographed on silica gel (eluant methylene chloride/acetone (60/40+1% triethylamine) to afford 70 mg of the title compound.

EXAMPLE 10

1-[3-oxy-androst-4-ene-17β-carbonyl]-1-sec-butyl-3-ethylurea

A mixture of 17β-(N-sec-butylcarbamoyl)-androst-4-en-3-one (300 mg) in anhydrous toluene (6 ml) and ethylisocyanate (1.16 ml) is refluxed for 24 hours.

The reaction mixture is evaporated to give an oil which is dissolved in chloroform, washed several times with brine and dried over sodium sulphate.

The solvent is removed under vacuum and the crude compound is chromatographed on silica gel eluting with methylene chloride/acetone (90/10), so obtaining 150 mg of the title compound.

What is claimed is:

1. A process for the preparation of a compound of formula (I)

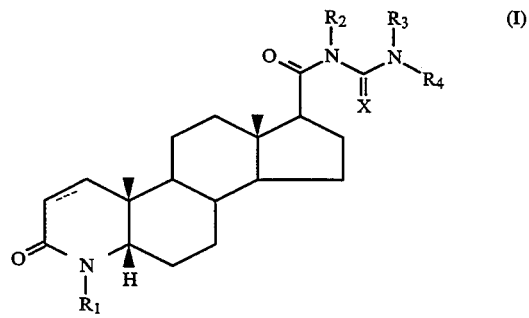

wherein X is oxygen or sulphur;

$R_1$ is hydrogen or $C_1$–$C_6$ alkyl;

each of $R_2$ and $R_3$ is, independently, hydrogen, $C_1$–$C_6$ alkyl, $C_5$–$C_6$ cycloalkyl or $C_6$–$C_9$ cycloalkylalkyl;

$R_4$ is hydrogen, $C_1$–$C_6$ alkyl, $C_5$–$C_6$ cycloalkyl, $C_6$–$C_9$ cycloalkylalkyl or aryl; and the symbol represents a single or a double bond; the process comprising the steps of:

a) oxidizing a compound of formula (II)

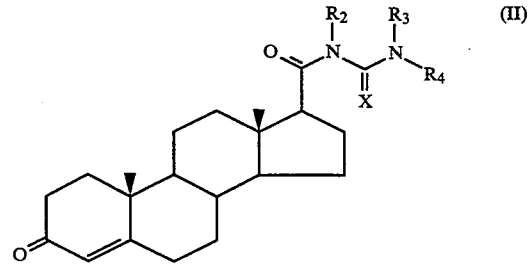

wherein X, R₂, R₃ and R₄ are as defined above, to obtain a compound of formula (III)

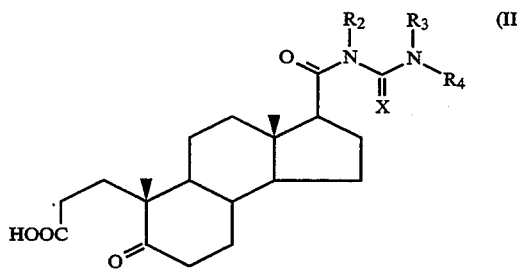

wherein X, R₂, R₃, and R₄ are as defined above;

b) reacting a compound of formula (III), as defined above, with a compound of formula (IV)

wherein R₁ is as defined above, to obtain a compound of formula (V)

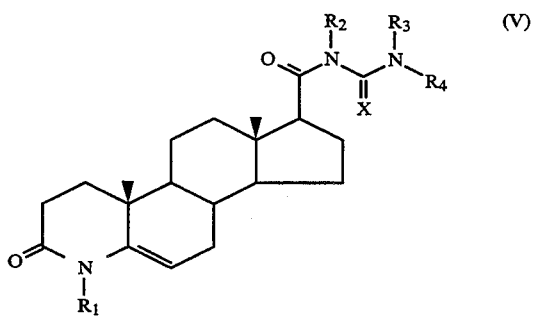

wherein X, R₁, R₂, R₃ and R₄ are as defined above;

c) reducing a compound of formula (V), as defined above, to obtain a compound of formula (I) wherein - - - - is a single bond and X, R₁, R₂, R₃ and R₄ are as defined above; and d) optionally dehydrogenating a compound of formula (I) wherein - - - - is a single bond and X, R₁, R₂, R₃ and R₄ are as defined above to obtain a compound of formula (I) wherein - - - - is a double bond and X, R₁, R₂, R₃ and R₄ are as defined above.

2. A process according to claim 1 wherein R₁ is hydrogen or a methyl or ethyl group, each of R₂ and R³ is, independently, hydrogen or a methyl, ethyl, isopropyl, tert-butyl, tert-butylmethyl, cyclohexyl or cyclohexylmethyl group; and R₄ is hydrogen or a methyl, ethyl, isopropyl, n-butyl, isobutyl, tert-butyl, tert-butylmethyl, cyclohexyl, cyclohexylmethyl, phenyl or 2,6-dichlorophenyl group.

3. A process according to claim 1 wherein the oxidation step (a) is carried out either in the presence of sodium metaperiodate and potassium permanganate in an organic solvent and aqueous potassium carbonate or in the presence of ozone in an organic solvent and then adding an oxidizing agent to destroy the resulting ozonide to the reaction mixture.

4. A process according to claim 1 wherein step (b) is carried out in an anhydrous organic solvent at a temperature from 60° C. to the reflux temperature of the solvent.

5. A process according to claim 1 which comprises performing steps (a) and (b) by reacting the compound of formula (II) with ozone in an organic solvent and adding to the resulting ozonide-containing reaction mixture the compound of formula (IV) to produce the compound of formula (V) directly.

6. A process according to claim 1 wherein the reduction step (c) is carried out in an organic solvent under a hydrogen pressure of from 101 to 1010 kPa (1 atm to 10 atm) in the presence of a hydrogenation catalyst.

7. A process according to claim 1 wherein the optional dehydrogenation step (d) is carried out in an anhydrous organic solvent in the presence of a dehydrogenating agent selected from chloranyl benzenselenic anhydride and dichlorodicyanobenzoquinone at a temperature of from room temperature to the reflux temperature of the solvent.

8. A process for preparing a compound of formula (I) as defined in claim 1, comprising the steps of reacting a compound of formula (III) as defined in claim 1 with a compound of formula (IV) as defined in claim 1; reducing the resulting compound of formula (V) as defined in claim 1 to obtain a said compound of formula (I) wherein is a single bond and X, R₁, R₂, R₃ and R₄ are as defined in claim 1; and, if desired, dehydrogenating the said compound of formula (I) in which is a single bond to obtain a corresponding compound of formula (I) wherein 'is a double bond and X, R₁, R₂, R₃ and R₄ are as defined above.

* * * * *

UNITED STATES PATENT AND TRADEMARK OFFICE
CERTIFICATE OF CORRECTION

PATENT NO. : 5,342,948
DATED : August 30, 1994
INVENTOR(S) : Achille PANZERI, et al.

It is certified that error appears in the above-indentified patent and that said Letters Patent is hereby corrected as shown below:

On the title page, Item[87] was omitted from the patent. It should read as follows:

--[87]   PCT Pub. No.:    WO93/02096
         PCT Pub. Date:   February 4, 1993--

Signed and Sealed this

Twenty-ninth Day of November, 1994

Attest:

BRUCE LEHMAN

*Attesting Officer*          *Commissioner of Patents and Trademarks*